US 6,589,172 B2

(12) United States Patent
Williams et al.

(10) Patent No.: US 6,589,172 B2
(45) Date of Patent: Jul. 8, 2003

(54) SWITCHING DEVICE FOR AN ARRAY OF MULTIPLE MEDICAL SENSORS

(76) Inventors: Glenn Williams, 405 18th Ave. NE., St. Petersburg, FL (US) 33704; Bill Williams, 3848 S. Rockbridge Rd., Stone Mountain, GA (US) 30087

( * ) Notice: Subject to any disclaimer, the term of this patent is extended or adjusted under 35 U.S.C. 154(b) by 57 days.

(21) Appl. No.: 09/932,516

(22) Filed: Aug. 17, 2001

(65) Prior Publication Data

US 2001/0051767 A1 Dec. 13, 2001

Related U.S. Application Data

(63) Continuation-in-part of application No. 09/586,925, filed on Jun. 5, 2000.

(51) Int. Cl.[7] ................................................. A61B 5/00
(52) U.S. Cl. ........................................ 600/309; 600/340
(58) Field of Search ................................ 600/309–310, 600/322–324, 340; 356/39–42

(56) References Cited

U.S. PATENT DOCUMENTS

| | | | | |
|---|---|---|---|---|
| 4,869,254 A | * | 9/1989 | Stone et al. ................ 600/336 |
| 5,271,403 A | * | 12/1993 | Paulos ........................ 600/443 |
| 5,282,464 A | * | 2/1994 | Brain ......................... 600/323 |
| 5,456,255 A | * | 10/1995 | Abe et al. ................... 600/443 |
| 5,627,531 A | * | 5/1997 | Posso et al. ................. 341/22 |
| 5,938,593 A | * | 8/1999 | Ouellette .................... 600/300 |

FOREIGN PATENT DOCUMENTS

| EP | 0290278 A1 | * | 9/1988 | ............ A61B/5/00 |
|---|---|---|---|---|
| JP | 60-232132 | | * 11/1985 | ............ A61B/5/14 |

* cited by examiner

Primary Examiner—Eric F. Winakur
Assistant Examiner—Matthew J Kremer
(74) Attorney, Agent, or Firm—Larson & Larson, PA; James E. Larson

(57) ABSTRACT

A switching device is interposed between a conventional physiological information monitor and a plurality of conventional sensors for a particular physiological function. The sensors are located on different parts of the body. Each of the plurality of sensors may be selected through the switching device to give a continuous indication of a particular physiological function in a localized area of the body. The device prevents the loss of information due to interrupted blood flow in a particular part of the body or the failure of a sensor.

9 Claims, 4 Drawing Sheets

SWITCHING DEVICE FOR AN ARRAY OF MULTIPLE MEDICAL SENSORS

This application is a continuation-in-part of application Ser. No. 09/586,925 filed Jun. 5, 2000.

FIELD OF THE INVENTION

This invention relates to a switching device for manually or automatically selecting a certain signal among a plurality of signals generated by a plurality of medical sensors. In certain situations, a patient may be simultaneously monitored at various locations for the same physiological information. The switching device of this invention allows the attending medical staff to read the various outputs from the various sensors by selecting the desired information source.

BACKGROUND OF THE INVENTION

The use of multiple sensors is conventional in the medical field. Usually each sensor has it's own discrete instrument for reading or otherwise obtaining the information produced by the sensor. In one situation several physiological parameters are being measured simultaneously and in a second situation the same parameter is measured at various points on the patient's body for comparison. In a third situation there may be multiple sensors collecting the same information simultaneously with other sensors collecting different information. Conventionally, in these situations there are lines from each sensor to each monitor. This quickly deteriorates into confusion and clutter about the patient.

Exemplary of this invention are transcutaneous oxygen ($O_2$) and carbon dioxide ($CO_2$) sensors, pulse oximetry sensors, such as disclosed in Ser. No. 09/586,925, incorporated herein by reference, blood pressure cuffs, arterial pressure lines (A lines), and airway pressure lines. Each of these different sensors has a particular lead for presenting the specific data in a standard form. The switching device has at least two ports for each of these leads.

Any or all of these sensors may be used in the operating room (OR) and the intensive care unit (ICU), as well as, in other applications, to provide information regarding the oxygen and/or carbon dioxide levels in a patient's blood, temperature, blood pressure, airway pressure and arterial pressure.

In transcutaneous sensors, for example, gas exchange between the blood and the skin results from oxygen diffusing out of capillaries and migrating outwardly through the stratum corneum to the atmosphere. The partial pressure of oxygen can be measured, noninvasively, at the skin surface.

A conventional transcutaneous oxygen sensor is made up of a modified polarographic Clark electrode which includes an anode and cathode of noble metals, an electrolyte, a semipermeable membrane, and a heating element. The heating element increases skin temperature and increases blood supply thereby increasing oxygen diffusion. The heating element may be controlled by thermistors set for high and low temperatures.

As the oxygen passes through the skin, it diffuses through the semipermeable membrane and dissolves in the electrolyte. The voltage between the cathode and anode converts the oxygen to hydroxyl ions. The current generated by this reaction is directly proportional to the partial pressure of oxygen in the underlying tissues. A processor receives the current and converts it to millimeters of Mercury, line graph, bar graph or other symbols and displays it on a monitor or print out.

Carbon dioxide is generated in the tissues adjacent the surface of the skin as a by-product of cellular metabolism and diffuses across the skin. The partial pressure of the carbon dioxide can be measured by a transcutaneous sensor. A conventional carbon dioxide sensor is made up of a Severinghaus pH electrode, a reference electrode, an electrolyte solution, a semipermeable membrane and a heating unit. The diffusing carbon dioxide passes through the semipermeable membrane adhered to the skin and into a dilute bicarbonate solution. The pH of the solution is lowered by the $CO_2$ and the glass electrode measures the change. The electrode output is processed to a signal recorded directly as the partial pressure of $CO_2$. The monitor shows the value on a digital display or other recording devices.

There are conventional transcutaneous sensors that measure both $O_2$ and $CO_2$. Such sensors are associated with monitors/processors that measure both $O_2$ and $CO_2$. Usually, these sensors and monitors are composites of each of the devices described above incorporated into one shell or one cabinet.

Conventionally, one transcutaneous sensor, whether an $O_2$ or $CO_2$ sensor, is associated with a single monitor as a single system. If a problem occurs in either the sensor or the processor, the entire system is replaced with another system. The same is true of the other sensor/monitor combinations mentioned above.

It is especially important to maintain a sterile field in the OR and the ICU. The equipment used in these locations should be sterile, also. The oxygen and carbon dioxide levels in the patient's blood are constantly monitored, along with blood pressure, temperature and breathing to determine the patient's well being in both these settings.

In certain situations in the OR, during surgery, blood flow in a particular part of the body may be interrupted or shunted into other fields. Such an event may cause the interruption of the sensor readings, if the system is located on an extremity in the affected part of the body. To immediately reestablish this vital information, the sterile field may be invaded to place another system on the body or to move the affected system to another suitable location on the patient. Using the switching device of this invention, another sensor, already in place, is selected without disturbing the sterile field.

This situation may also occur in the ICU. Also, in the ICU the patient may cause the sensors to become dislodged through body movement. Of course, there are other mechanical reasons that a system may malfunction and require replacement. This important information concerning the patient's vital signs is lost during the period of time required to position a new system. Using the switching device of this invention the flow of information can be re-established by moving a selector.

In wound care situations, for example, multiple sensors are used to map the $O_2$ levels in particular areas of the body. For example, if there are sores or wounds that are slow to heal, due in part to poor circulation, the blood oxygen level is useful in determining the ability of the wounds to heal. Normally 3 to 5 sites are used to give an indication of the situation in the particular area of the body and to compensate for any anomaly at any sensor. Conventionally, this mapping requires 3 to 5 processors. With the present equipment, readings from the various locations may be gathered and compared by moving the selector.

One side effect of the transcutaneous sensors, in particular, results from the use of the heating ring which increases blood flow at the sensor. Varying degrees of burns may result in thin skinned infants and adults with peripheral vascular impairment. Frequent sensor relocation, as recommended by the manufacturer, alleviates this side effect. However, relocation may require recalibration and there may be a 30 minute period necessary to stabilize the sensor on the new site. By rotating the activation of the sensors, the heat build-up at each sensor is shortened.

Thus, what is needed in the art is an apparatus that will provide continuous readings of several vital signs without disturbing the patient or the sterile field when blood flow to a particular part of the body is interrupted or a sensor fails. Also, when mapping an area of the body, different sensors, already in place, may be sampled sequentially or in a random fashion and displayed on a single monitor.

DESCRIPTION OF THE PRIOR ART

U.S. Pat. No. 5,957,854 issued to Bessom et al, Sep. 28, 1999, teach the conventional use of multiple sensors wired to a monitor for EKG readings. The patent replaces the multiple wires with wireless sensors having antennae.

U.S. Pat. No. 5,279,297, issued to Wilson et al, U.S. Pat. No. 5,501,225 issued to Wilson Mar. 26, 1996 and U.S. Pat. No. 5,593,899 issued to Wilson et al on Jan. 14, 1997 all teach the use of a phosphorescent dye in the body with a light guide needle inserted in different parts of the body to excite the dye thereby mapping oxygen levels in portions of the body. However, the mapping results from multiple sequential placement and removal of the needle in different parts of the body.

SUMMARY OF THE INVENTION

It is an object of this invention to provide a switching device interposed between several sensors sensing physiological parameters and a display to present the information from the sensor selected.

It is an object of this invention to provide a switching device interposed between several transcutaneous sensors, or several oximetry sensors, or several blood pressure cuffs, or several airway passage pressure lines, or several arterial pressure lines and a conventional display to present the information from the sensor selected.

It is an object of this invention to provide a switching device interposed between a single display and a plurality of transcutaneous $O_2$, $CO_2$ or combination $O_2$ and $CO_2$ sensors located at various sites on the body. The switching device may be operated in a manual mode wherein each sensor may be individually selected to provide the input signal to the multiple function display. The device prevents the loss of partial pressure oxygen and/or partial pressure carbon dioxide information due to interrupted blood flow in a particular part of the body or the failure of a sensor.

It is an objective of this invention to provide an array of stabilized transcutaneous sensors on the body connected to a switching device and one display to map the blood oxygen and/or carbon dioxide levels in a particular area.

It is a further objective of the invention to provide an array of stabilized transcutaneous sensors connected to a switching device and one display for sequential activation to lessen heat build-up at the sensor site.

It is another objective of this invention to provide a switching device interposed between the array of transcutaneous sensors and the display for selection of a particular incoming signal from one of the sensors.

It is yet another objective of this invention to provide the switching device with a manual mode and an automatic mode of operation.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 5:
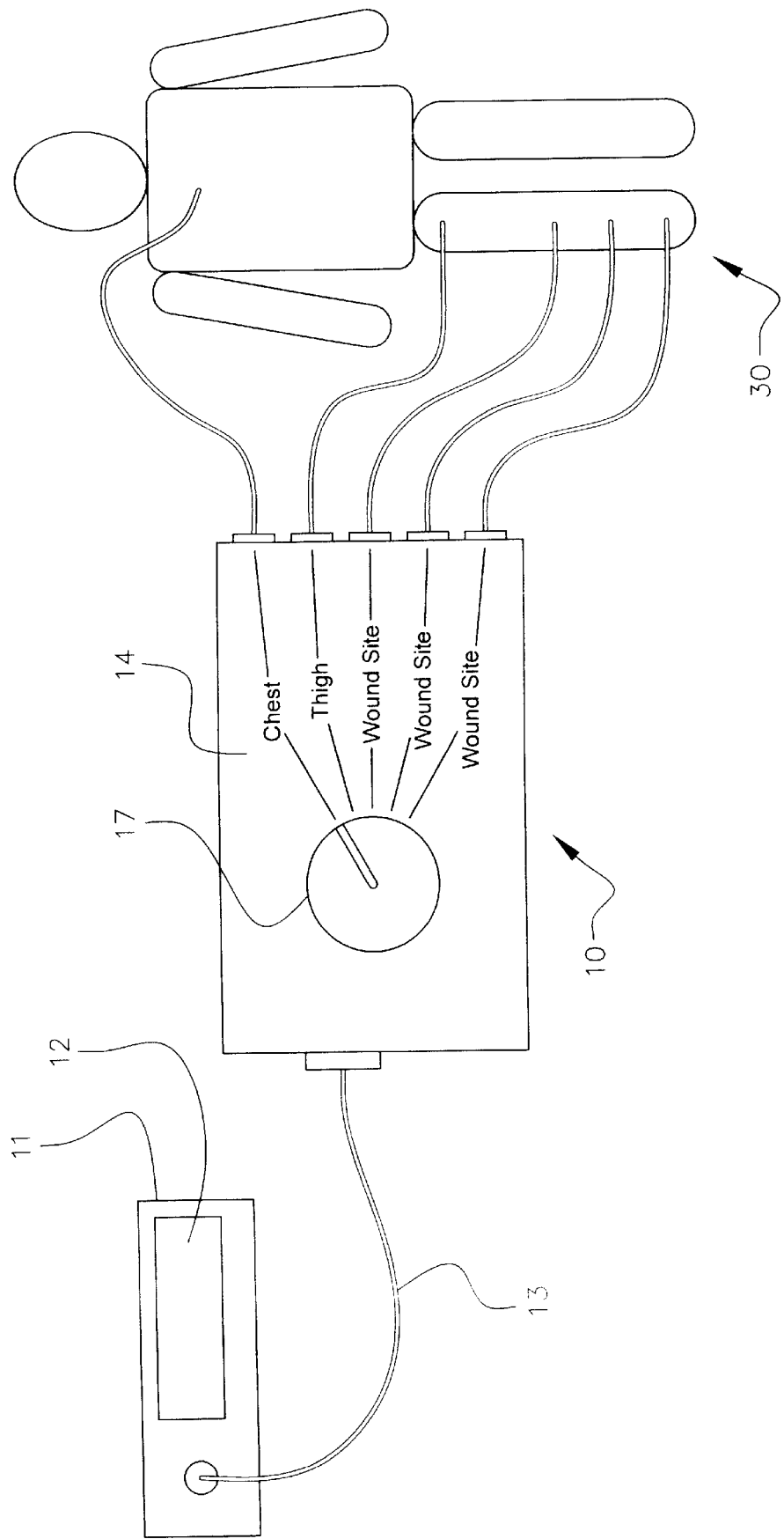
FIG. 5 shows a block diagram of the switching device, a monitor and an array of transcutaneous sensors.

Using an array of transcutaneous sensors, as an example, the switching device 10 is shown operatively connected to an processor/monitor 11 by output cable 13, in FIG. 5. The processor/monitor section 11 and display 12 are well known in the art and operate to alternately energize the sensors 30 and to calculate and display the partial pressure oxygen value from a transcutaneous sensor 23, shown in FIG. 2.

Figure 6:
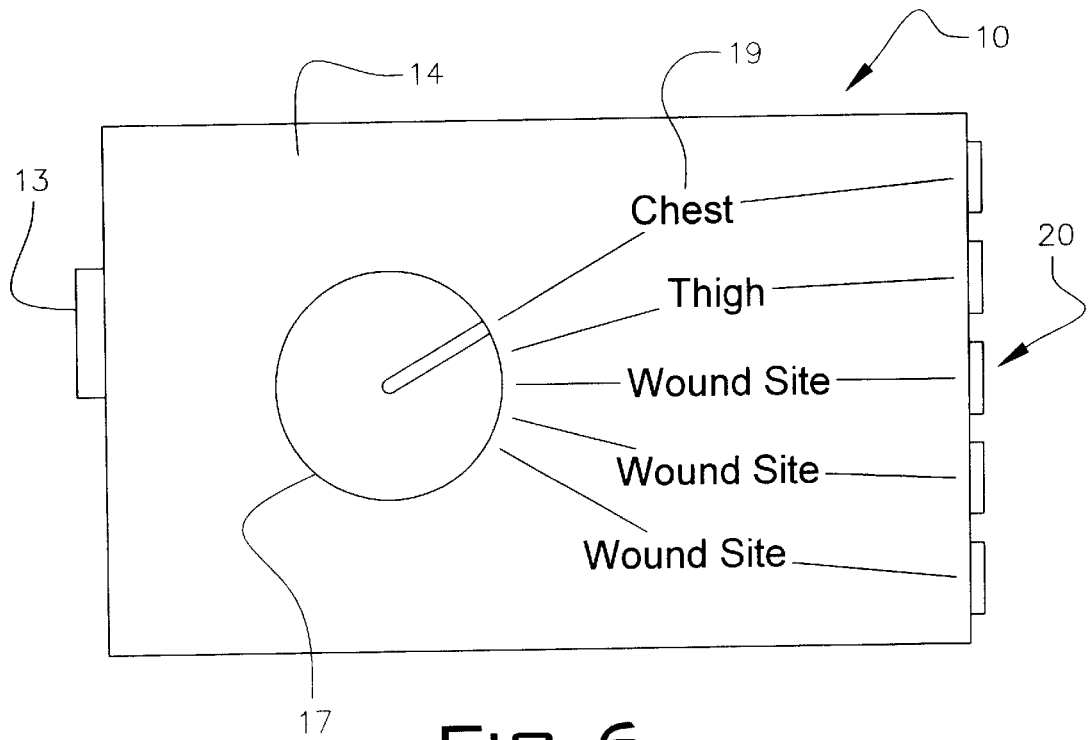
FIG. 6 shows a block diagram of the switching device with a manual switch.

The switching device 10 is illustrated in the general form of a rectangular housing 14, though the exact shape is of no moment. On one surface of the housing 14 there is a rotary selector knob 17. The selector knob 17 may be manually placed in any one of several positions as indicated about the circumference of the knob, by rotating the knob. As seen in FIG. 6, sensor position 19, labeled Chest, is selected.

As shown in FIG. 5, the input connections 20 each go to an individual transcutaneous sensor located on a part of the body as labeled on the face of the box 14. The transcutaneous sensor may be a conventional $CO_2$ sensor, as shown in FIG. 1, an $O_2$ sensor, as shown in FIG. 2, or a combination oxygen and carbon dioxide sensor, shown in FIG. 3.

Figure 1:
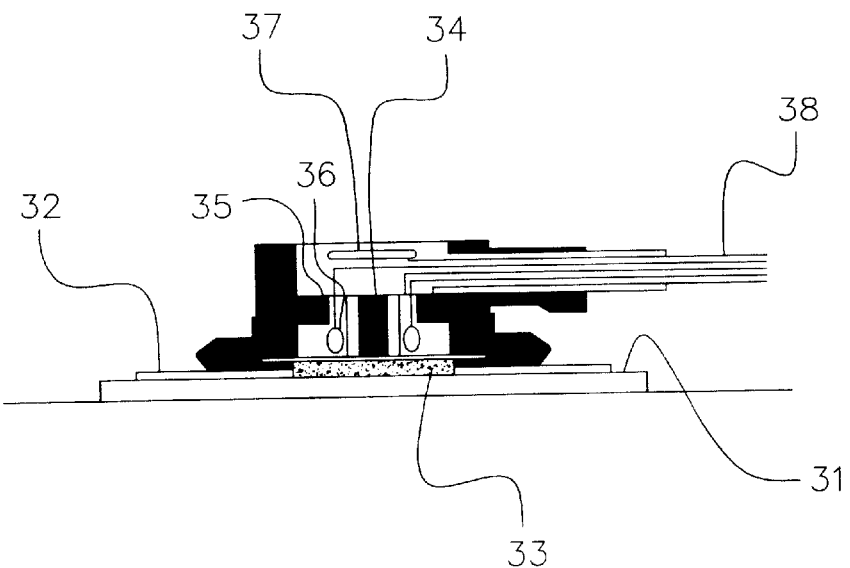
FIG. 1 shows a cross section of a conventional transcutaneous carbon dioxide sensor.
Figure 2:
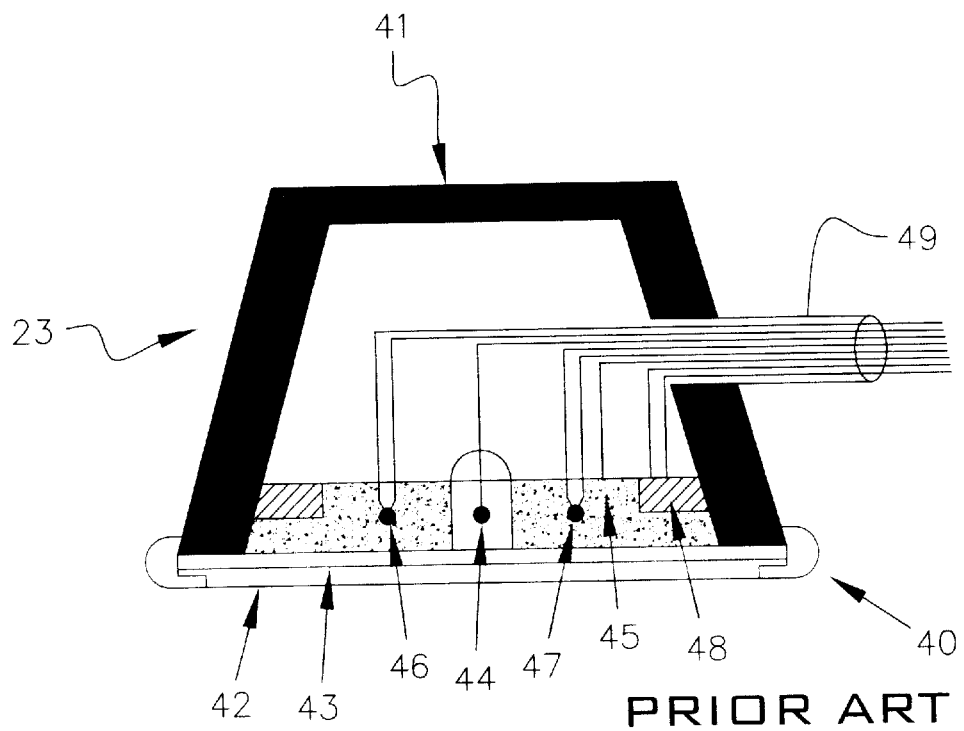
FIG. 2 shows a cross section of a conventional transcutaneous oxygen sensor.
Figure 3:
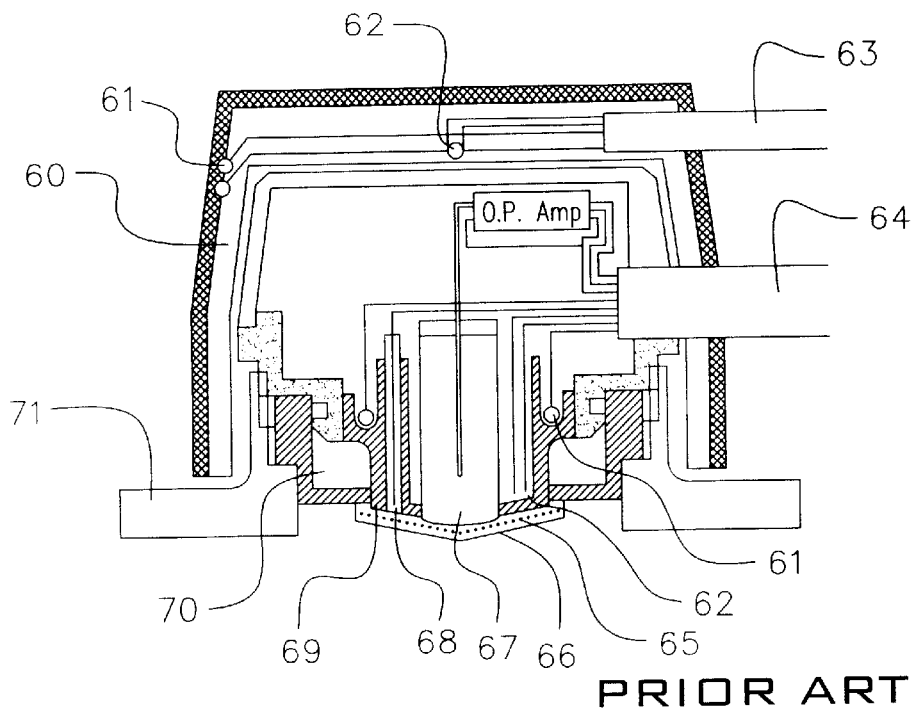
FIG. 3 shows a cross section of a conventional combination $O_2$ and $CO_2$ transcutaneous sensor.
Figure 4:
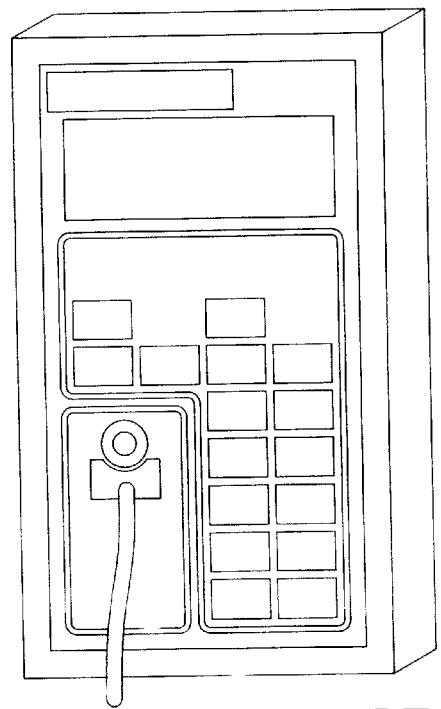
FIG. 4 shows a perspective of a conventional transcutaneous monitor.

In normal operation, the transcutaneous sensors shown in FIGS. 1, 2, and 3 are each, singularly, connected to a transcutaneous monitor such as shown in FIG. 4.

There are situations, as in the case of reattachment of extremities, in which the array of transcutaneous sensors may be placed on the different digits of the same hand or foot. In this manner, the blood flow to the reattached hand or foot could be monitored in each finger or toe of that extremity merely by switching the knob to the different positions.

As shown in FIG. 5, an array of transcutaneous sensors may be placed on the leg of a patient to map the blood oxygenation levels at various locations in the leg. The $O_2$ level is directly related to blood flow in those locations so that areas of poor blood flow may be determined and, if necessary, corrected. Reference sensors may be placed at other locations, such as the chest and/or thigh for comparison data.

Figure 7:
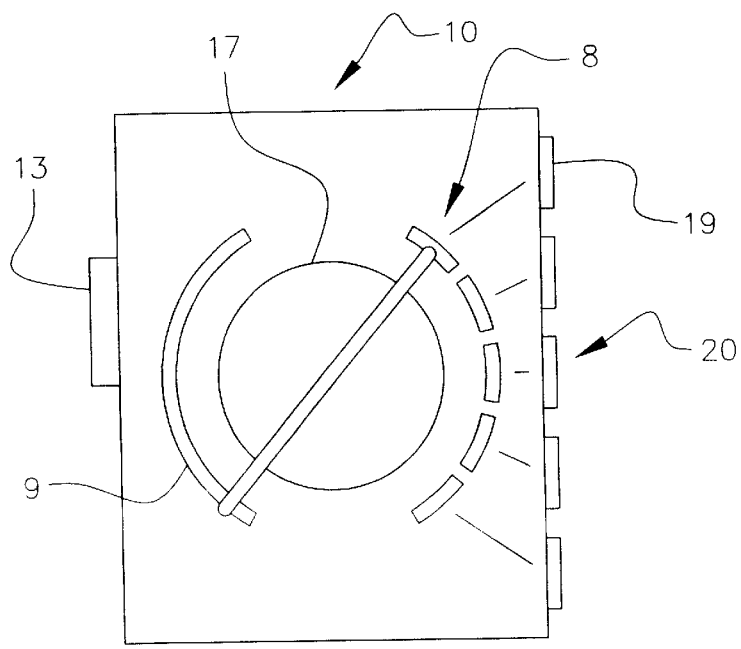
FIG. 7 shows a block diagram of a manual switch.

FIG. 7 shows a representation of a manual switch with separate electrical leads 8 from each of the multiple sensors 20 capable of being sequentially engaged by the selector knob 17 while the knob is continuously connected to the cable 13. The selector knob 17 may be electrically powered and directed by computer. With an electrically powered selector knob, a remote monitor and controller may be used where a particular sensor may be selected and the $O_2$ or $CO_2$ level can be read for that sensor.

A conventional electrochemical $CO_2$ sensor, shown in FIG. 1, has an adhesive ring 31, a membrane 32, a solution 33, a pH sensitive glass electrode 34, a reference electrode 35 thermistors 36, and a buffer amplifier 37. The resulting signal is transmitted to the monitor by cable 38.

The conventional $O_2$ transcutaneous sensor of FIG. 2 has an adhesive retaining ring 40 which attaches the shell 41 to the patient. The semipermeable membrane 42 is in intimate contact with the skin. After the gas passes through the membrane, it contacts an electrolyte 43. The electrolyte is in contact with a cathode 44 and an anode 45. High temperature and low temperature thermistors 46 and 47 track the performance of the heating ring 48. These components are connected to the monitor by cable 49.

A conventional combination electrochemical sensor of FIG. 3 has a foam covered aluminum housing 60 enclosing a heaters 61, thermistors 62, $O_2$ cable 63, $CO_2$ cable 64, electrolyte 65, semipermeable membrane 66, glass electrode 67, $O_2$ cathode 68, heated reference electrode 69, $CO_2$ electrolyte 70, and an adhesive pad 71.

Each of the transcutaneous sensors, described above, conventionally has its own monitor attached to the cable. The combination sensor has two monitors with different functions. This creates a maze of wires connecting the sensors with the monitors.

The switching device of this invention allows the transcutaneous sensors to be connected to the switching device in close proximity to the patient. The single monitor for all the sensors may be at some distance removed and connected by one cable.

A similar switching device may be used in other instances, noted above, to reduce the number of displays or indicators to a single device while providing the flexibility of collecting information from several sensors located at different sites. For example, a patient may be fitted with more than one blood pressure cuff with a lead line from each cuff to a switching device. A single pressure line would connect the switching device with a single sphygmometer. Another example is a patient fitted with multiple temperature probes with a lead line from each probe to a switching device, as disclosed. One temperature indicator is connected to the switching device to read the selected probe temperature.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A method of providing a continuous indication of a particular physiological function in a localized area of a body, said method comprising the steps of:
   a) providing a monitor which produces a display of particular physiological information, said monitor having a plurality of transcutaneous sensors, said transcutaneous sensors adapted to be temporarily connected to the body;
   b) mounting each of said transcutaneous sensors on a different part of the body;
   c) connecting a switching device to said monitor and said plurality of transcutaneous sensors, said switching device having a selector, said selector having multiple positions, each of said positions connecting one of said transcutaneous sensors and conveying the particular physiological information to said monitor;
   d) selecting one of said positions with said selector; and
   e) reading said indication of said particular physiological information from said monitor.

2. A method of providing a continuous indication of a particular physiological function according to claim 1 wherein each of said transcutaneous sensors is activated on a continuous basis whereby instantaneous sensor readings are obtained upon selector switch positioning to provide a continuous indication of a blood oxygenation function in a localized area of the body.

3. A method of providing continuous blood oxygenation readings, said method comprising the steps of:
   a) providing a monitor which produces said readings, said monitor having a plurality of transcutaneous sensors, said transcutaneous sensors adapted to be temporarily connected to a body;
   b) mounting each of said transcutaneous sensors on a different part of the body;
   c) connecting a switching device to said monitor and said plurality of transcutaneous sensors, said switching device having a selector, said selector having multiple positions, each of said positions electrically coupled to one of said plurality of transcutaneous sensors and conveying the return signal to said monitor;
   d) selecting a particular position and activating said transcutaneous sensor by operation of said selector; and
   e) producing a blood oxygenation reading from said selected transcutaneous sensor.

4. A method of providing continuous blood oxygenation readings of claim 3 and determining localized blood flow from said blood oxygenation reading to provide an indication of a particular physiological function in a localized area of the body.

5. A method of providing continuous blood oxygenation readings of claim 3 including providing said selector with a selector knob denoting a position of one of said transcutaneous sensors.

6. A method of providing continuous blood oxygenation readings of claim 5 including the step of manually selecting a particular position.

7. A method of providing continuous blood readings oxygenation according to claim 3 wherein each of said transcutaneous sensors is activated on a continuous basis whereby instantaneous sensor readings are obtained upon selector switch positioning to provide a continuous indication of a particular physiological function in a localized area of the body.

8. A switching device for a blood oxygen monitor having plural transcutaneous sensors, said switching device comprising a housing, said housing including an output connection adapted for communication to said oxygen monitor and a plurality of input connections each adapted for communication with one of said plural transcutaneous sensors, a selector carried by said housing for selectively connecting a particular input connection to said output connection, and a plurality of indicators on said housing for showing which of said input connections is active.

9. A switching device of claim 8 wherein said selector is rotary and said plurality of indicators are mounted on said housing about the circumference of said rotary selector.

* * * * *